(12) United States Patent
Hebecker et al.

(10) Patent No.: US 7,050,531 B2
(45) Date of Patent: May 23, 2006

(54) METHOD FOR INTRAOPERATIVE GENERATION OF AN UPDATED VOLUME DATASET

(75) Inventors: Axel Hebecker, Spardorf (DE); Matthias Mitschke, Nuremberg (DE); Norbert Rahn, Forchheim (DE); Dieter Ritter, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 106 days.

(21) Appl. No.: 10/675,301

(22) Filed: Sep. 30, 2003

(65) Prior Publication Data

US 2004/0131156 A1 Jul. 8, 2004

(30) Foreign Application Priority Data

Sep. 30, 2002 (DE) ................................. 102 45 670

(51) Int. Cl.
*A61B 6/03* (2006.01)

(52) U.S. Cl. ............................... 378/8; 378/4; 378/901
(58) Field of Classification Search .................. 378/4, 378/8, 15, 19, 22, 23, 901
See application file for complete search history.

(56) References Cited

U.S. PATENT DOCUMENTS

| | | | | |
|---|---|---|---|---|
| 5,841,830 A | * | 11/1998 | Barni et al. | .................... 378/15 |
| 6,470,070 B1 | * | 10/2002 | Menhardt | ...................... 378/62 |
| 6,577,889 B1 | * | 6/2003 | Ichihashi | ..................... 600/425 |
| 2001/0029334 A1 | | 10/2001 | Graumann et al. | |
| 2004/0120469 A1 | * | 6/2004 | Hebecker et al. | ............ 378/210 |

FOREIGN PATENT DOCUMENTS

| | | |
|---|---|---|
| DE | 0S19807884 | 9/1999 |
| EP | 0860144 | 8/1998 |

* cited by examiner

*Primary Examiner*—David V Bruce
(74) *Attorney, Agent, or Firm*—Schiff Hardin LLP

(57) ABSTRACT

In a method for the intraoperative generating of an updated volume dataset, a first volume dataset is reconstructed from a series of n 2D X-ray projections (of a patient that are acquired at different angles. During a medical intervention, m 2D X-ray projections (m<n) of the patient are acquired from different angles. In a first version of the method, m 2D X-ray projections of the series of n 2D X-ray projections are replaced by the intraoperatively acquired m 2D X-ray projections, and an updated volume dataset is reconstructed using the intraoperatively acquired m 2D X-ray projections and n–m 2D X-ray projections that were not replaced in the series of n 2D X-ray projections. In a second version of the method, a second volume dataset is reconstructed with the intraoperatively acquired m 2D X-ray projections and is fused with the first volume dataset to form an updated volume dataset.

26 Claims, 3 Drawing Sheets

METHOD FOR INTRAOPERATIVE GENERATION OF AN UPDATED VOLUME DATASET

BACKGROUND OF THE INVENTION

1. Field of the Invention

The invention concerns methods for intraoperative generation of an updated volume dataset of a patient.

2. Description of the Prior Art

In the course of a medical procedure on a patient, in particular a minimally invasive procedure, it is frequently necessary to monitor position changes of biological tissue in the patient by means of diagnostic X-ray imaging. Such a requirement exists, for example, in the case of complicated fractures, in particular multiple fractures with a number of small bone fragments with complex morphology, which in the osteosynthesis must be aligned and set relative to one another. Conventionally, the repositioning of the bone fragments and their subsequent setting ensue using individual 2D X-ray projections, and the surgeon during the minimally invasive procedure must mentally reconstruct the three-dimensional anatomical situation in reality from the 2D X-ray projections acquired at different viewing angles. This mental 3D reconstruction of the real three-dimensional anatomical situation from a number of 2D X-ray projections acquired intraoperatively requires a great deal of experience, imagination, and concentration on the part of the surgeon.

It also is possible to generate, with a C-arm X-ray device, a volume dataset containing image information about the bone fragments at definite points in time after the positioning of the patient. To product the volume dataset a series of 2D X-ray projections is acquired at various projection angles. The surgeon would prefer to undertake the osteosynthesis using such volume data generated intraoperatively, from which 2D or 3D images can be generated. This is not currently possible because the 3D image data do not represent an image that is sufficiently current, since a frequent or even continuous complete intraoperative update of the 3D image data during the continuous repositioning of the bone fragments is not possible, both due to time considerations and due to radiation protections considerations.

SUMMARY OF THE INVENTION

An object of the present invention is to provide a method to intraoperatively generate an updated volume dataset with the least possible radiation exposure for the patient.

This object is achieved in a first embodiment of the inventive method wherein a series of n 2D X-ray projections of the patient is achieved from n different angles with an X-ray system prior to a medical intervention on the patient but after the patient has been positioned on a support device, a first volume dataset being reconstructed from said projections using known projection geometries that have been calculated in an offline calibration process or online during the patient measuring procedure, for example. During the intervention, m<n 2D X-ray projections of the patient are acquired from m different angles with the X-ray system, and their projection geometries are computed. In the series of n 2D X-ray projections, m 2D projections are replaced by these m intraoperatively acquired X-ray projections. An updated volume dataset is then reconstructed from the m intraoperatively acquired 2D X-ray projections and the n−m 2D X-ray projections that were not replaced, or a portion thereof, in the originally acquired series of 2D X-ray projections. The resulting updated volume dataset thus contains not only image information of the patient after her positioning but also timely image information that is acquired during a medical intervention. By this method, it is possible to reconstruct a volume dataset of the patient containing timely image information during a medical intervention after acquiring a few select 2D X-ray projections and therefore by applying a substantially smaller X-ray dose than would have to be applied for the repeated acquisition of an entire new series of n 2D X-ray projections, and in a substantially shorter time than is required for repeated acquisition of a new entire series of n 2D X-ray projections. Because of the small radiation load for the patient and the relatively short computing time, such updating of a volume dataset can be performed multiple times during a medical intervention.

Thus, the first volume dataset contains image information from biological tissue of the patient in an initial position, and the updated volume set contains image information of the biological tissue of the patient in the initial position as well as after a position change of the tissue that occurs during a medical intervention. In order to be able better to distinguish the image information of the biological tissue in its initial situation from the image information of the tissue after its position change, the updated volume dataset can be modified so that the image information of the biological tissue in its initial position and the image information of the biological tissue after its position has changed are able to be visually differentiated from each other, i.e., are coded. This can be achieved by the first volume dataset being subtracted from the updated volume dataset, and the resulting third volume dataset, which contains substantially only image information of the biological tissue after its position has changed, being coded and fused with the first volume set, so as to form the modified updated volume dataset. The coding can be a gray scale coding or color coding, the original position and orientation of the biological tissue being represented in the modified updated volume dataset in gray scale coded form and the current position and orientation of the biological tissue during the intervention being represented in color coded form, for example.

In a further embodiment of the invention, the biological tissue is a bone fragment, or more usually a number of bone fragments, which must be aligned and set relative to one another in the framework of an osteosynthesis.

In an embodiment of the invention, in the intraoperative acquisition of one of the m 2D X-ray projections, the X-ray system occupies a position relative to the patient that is substantially the same as in the acquisition of one of the 2D X-ray projections of the series of n 2D X-ray projections. This has the advantage that the projection geometries for this intraoperatively acquired 2D X-ray projection correspond to the projection geometries of the corresponding 2D X-ray projection of the series of n 2D X-ray projections, and thus are subsequently already prepared and can immediately be used in the reconstruction of the updated volume dataset. According to variants of this embodiment of the invention, the X-ray system can be caused to occupy the aforementioned position by the X-ray system being automatically adjusted by motor or manually into such a position under supervision of angle or position transmitters, or using a mechanical arresting device.

Alternatively, the X-ray system in the intraoperative acquisition of one of the m 2D X-ray projections can occupy another position relative to the patient, as in the acquisition of a 2D X-ray projection of the series of n 2D X-ray projections. In this case, the projection geometries for this position of the X-ray system must either be determined in a separate calibration process before the patient measurement or calculated by means of interpolation from the known or determined projection geometries of the X-ray system. Also in this case, the projection geometries are known, so the updated volume dataset can be reconstructed from the intraoperatively acquired 2D X-ray projections and the aforementioned n–m 2D X-ray projections, or a portion thereof, that have not been replaced in the original series.

In a preferred embodiment of the invention, the X-ray system has a C-arm provided with an X-ray source and an X-ray radiation receiver. The C-arm preferably is isocentrically adjustable and is a component of a movable C-arm X-ray device.

The above object also is achieved in a second embodiment of the inventive method, wherein a first volume dataset is reconstructed using projection geometries that are known, for instance from an offline calibrating process, from a series of n 2D X-ray projections of a patient that are acquired at n different projection angles with an X-ray system subsequent to the positioning of the patient. Following the intraoperative acquisition of m 2D X-ray projections (wherein m<n) of the patient from m different angles by the X-ray system, a second volume dataset is reconstructed based on determined projection geometries for each of the m 2D X-ray projections, and the second volume dataset is fused with the first volume dataset to form an updated volume dataset. This represents another way in which the intraoperative acquisition of m 2D X-ray projections, the reconstruction of a second volume dataset from the intraoperative m 2D X-ray projections, and the subsequent fusing of that volume dataset with the originally acquired volume dataset, result in an updated volume dataset containing both image information of the patient in her initial situation and timely image information that is acquired during a medical intervention, so that the difference between the instantaneous situation and the initial situation is recognizable in the dataset to the surgeon who is conducting the medical intervention.

Thus, the first volume dataset contains image information of biological tissue of the patient in an initial position, the second volume dataset contains image information of the biological tissue of the patient after a change of position of the biological tissue, and the updated volume dataset contains image information of the biological tissue of the patient in its initial position and after the change of position. In this embodiment of the method as well, in order better to be able to distinguish the image information of the biological tissue in its initial position from the image information of the biological tissue after it has changed its position, the image information of the biological tissue in its initial position and the image information of the biological tissue after it has changed its position can be coded in the updated volume dataset. This can be accomplished by the image information of the biological tissue after the position change being coded in the second volume dataset prior to the fusion of the first volume dataset with the second volume dataset. As described in connection with the first embodiment, the coding can be a gray scale coding or color-coding.

As in the first embodiment, the biological tissue can be a bone fragment, or a number of bone fragments. Furthermore, according to variants of the invention, the X-ray system in an intraoperative acquisition of one of the m 2D X-ray projections can occupy a position relative to the patient that is substantially the same as in the acquisition of a 2D X-ray projection of the series of n 2D X-ray projections. In the acquisition of the m 2D X-ray projections, the X-ray system alternatively can occupy completely different positions, such that the projection geometries for these positions of the X-ray system must be determined in a calibration process or calculated by means of interpolation from known projection geometries.

According to a variant of the invention, the X-ray system (as described before) has a C-arm, provided with an X-ray source and an X-ray radiation receiver, which preferably is isocentrically adjustable and is a component (mobile) of a portable C-arm X-ray device.

DESCRIPTION OF THE PREFERRED EMBODIMENTS

Figure 1:
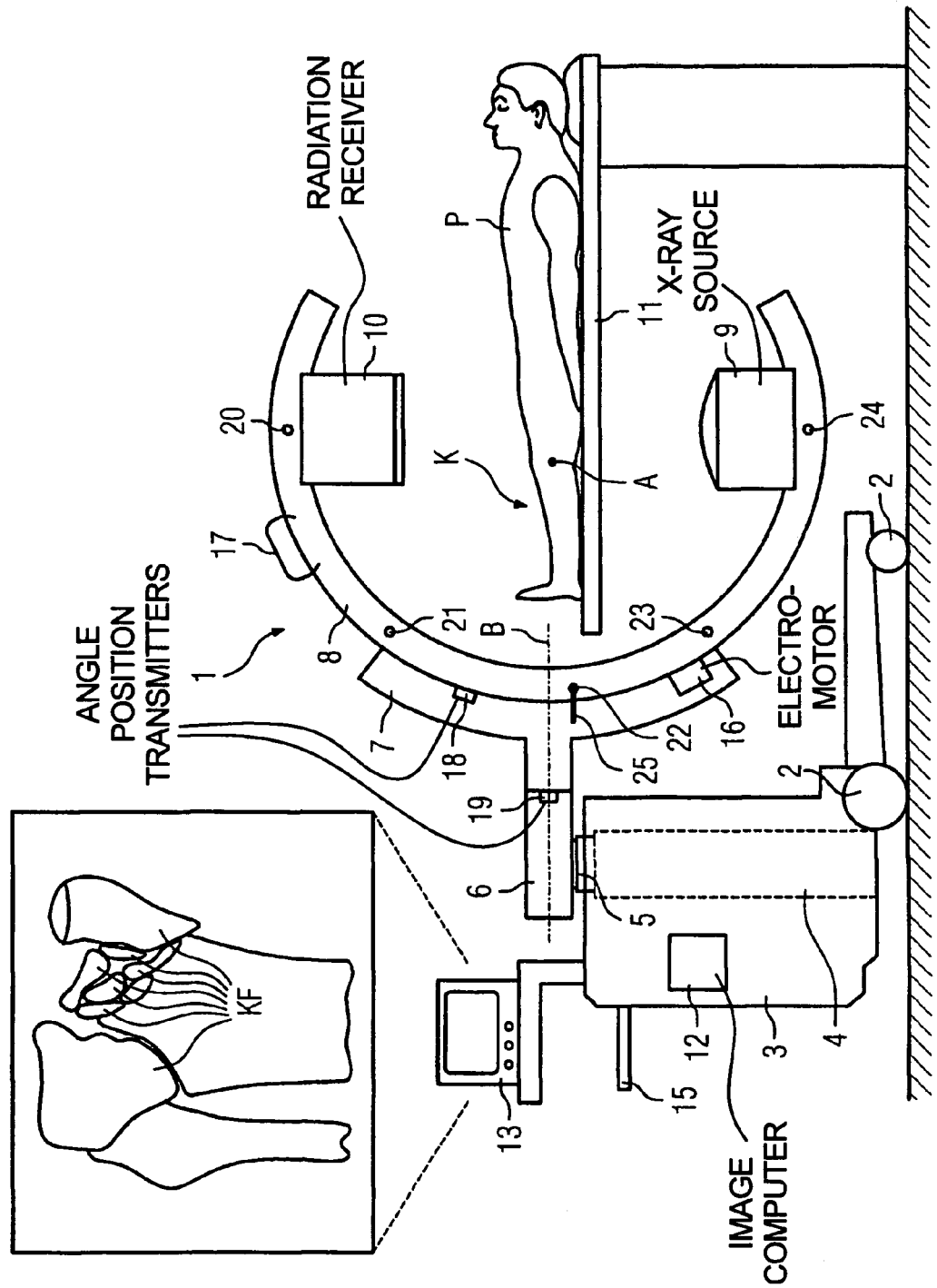
FIG. 1 shows a C-arm X-ray device to implement the inventive method.

The C-arm X-ray device 1 shown in FIG. 1 is suitable for implementing the inventive method and has a device cart 3, provided with wheels, in which is arranged a lifting device 4 (shown only schematically in FIG. 1) having a column 5. A holder 6 is arranged at the column 5 at which a positioner 7 is present to position a C-arm 8. An X-ray source 9 and an X-ray radiation receiver 10 are arranged opposite one another on the C-arm 8. The X-ray source 9 preferably emits a conical X-ray beam in the direction of the X-ray radiation receiver 10 (having a planar receiver surface), which can, for example, be an X-ray intensifier or a flat image detector. In the exemplary embodiment, the C-arm 8 can be isocentrically adjusted both around its orbital axis A (schematically indicated in the FIG. 1) and around its angulation axis B (schematically indicated in the FIG. 1).

Volume datasets, for example voxel volumes, can be generated with the C-arm X-ray device 1 representing body parts of a patient P positioned on a patient bed 11. In the exemplary embodiment, an image computer 12 is connected (in a manner not shown) in the cart 3 with the X-ray radiation receiver 10. The image computer 12 can reconstruct a volume dataset or voxel volume of the body part to be imaged, by back-projection in a known manner from a series of n 2D X-ray projections, are acquired by moving the C-arm 8 around a body part of the patient P to be shown in an image) while irradiating the body part with the X-ray source 9 and detecting the attenuated radiation with the X-ray radiation receiver 10. The C-arm 8 is either adjusted along its perimeter around the orbital axis A or adjusted around the angulation axis B through approximately 190°. During the movement approximately 50 to 200 2D X-ray projections are acquired. The projection geometries necessary for the reconstruction of a voxel volume were determined in a known manner using a calibration phantom in an offline calibration of the C-arm X-ray device 1, and stored in a memory (not shown) of the C-arm X-ray device 1, to which the image computer 12 has access. An offline calibration to determine the projection geometries can ensue, for example, with a calibration phantom as described in German OS 100 47 382 having X-ray positive marks.

Figure 2:
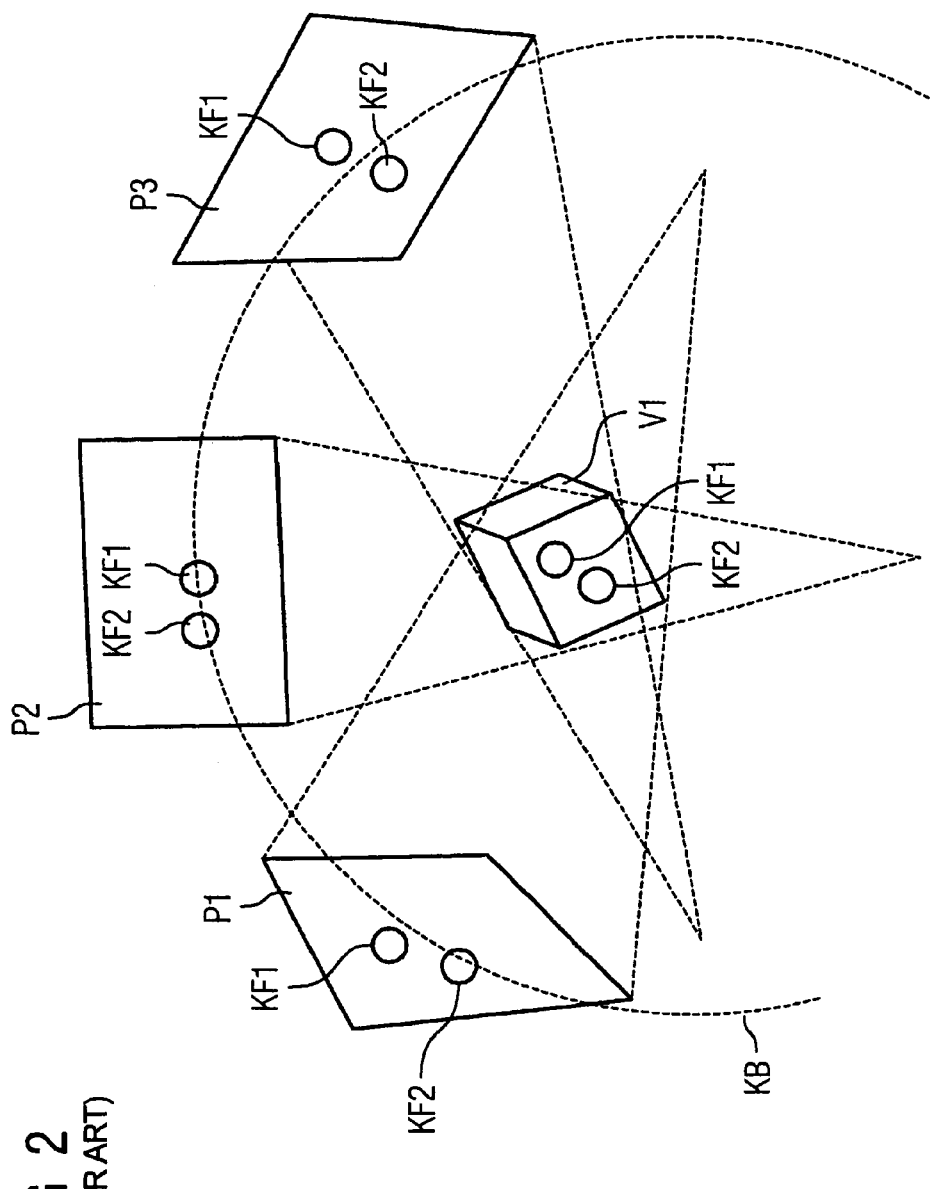
FIG. 2 schematically illustrates the reconstruction of a volume dataset from a series of n 2D X-ray projections.

In the exemplary embodiment, a series of n 2D X-ray projections is acquired with the C-arm X-ray device 1 of the knee region K of the patient P (who has sustained a multiple fracture in the knee region K) at n different projection angles after the positioning of the patient P on the patient bed 11, by moving the C-arm 8, together with the X-ray source 9 and the X-ray radiation receiver 10 around its orbital axis A through approximately 190°. In the image computer 12, a voxel volume of the knee region K of the patient P is reconstructed by back-projection from the series of n 2D X-ray projections and the projection geometries that were determined for this adjustment movement of the C-arm 8 and stored. In schematic depiction, FIG. 2 illustrates the acquisition of the n 2D X-ray projections by movement of the C-arm 8 on an orbit KB, as well as the back-projection to reconstruct the voxel volume V1. The exemplary 2D X-ray projections P1 through P3 shown in FIG. 2, as well as the reconstructed voxel volume V1, each contain two points that should show images KF1 and KF2 of bone fragments. While the depiction of the images KF1 and KF2 of the bone fragments is two-dimensional in the 2D X-ray projections, their representation in the voxel volume V1 is three-dimensional (in a manner that cannot be recognized from FIG. 2).

From this voxel volume V1, which is present in the image computer 12, 3D images or 2D images of the knee region K can be generated by a known method (for example the MPR method (mulitplanar reformation)) and are shown on a display device 13 connected (in a manner not shown) with the image computer 12. For example, an image approximating the real-time appearance (generated from the first voxel volume V1) of the multiple fracture in the knee region K of the patient P is shown. In this manner, a surgeon (not shown in FIG. 1) treating the patient P can obtain an impression of the multiple fracture in the knee region K of the patient P and plan the osteosynthesis, i.e. the repositioning of the individual bone fragments KF and their subsequent setting.

In order to graphically show, during the repositioning, bone fragments changed with regard to their position and orientation relative to the initial positions shown in FIG. 2, and thus to be able to aid the surgeon in the osteosynthesis, after position changes undertaken intraoperatively on the bone fragments, m intraoperative (m<n, for example m=5) 2D X-ray projections of the knee region K, and thus of the bone fragments of the patient P, are acquired at m different projection angles. For this purpose, the C-arm 8 is brought into the corresponding selected positions relative to the patient P. In the intraoperative acquisitions of the m 2D X-ray projections of the knee region K of the patient P, the C-arm 8 preferably occupy positions which substantially correspond to positions from which the 2D X-ray projections of the series of n 2D X-ray projections were already acquired. This allows the use of projection geometries for the intraoperative 2D X-ray projections that are already known and need not be additionally calculated. Accordingly, upon replacement of m 2D X-ray projections out of the series of n. 2D X-ray projections with the intraoperatively captured m 2D X-ray projections—a 2D X-ray projection of the series of n 2D X-ray projections generally being replaced by an intraoperative 2D X-ray projection that was acquired with the same C-arm position—an updated voxel volume can be reconstructed by means of the image computer 12 and the known projection geometries, based on the intraoperative m 2D X-ray projections and the n–m 2D X-ray projections, or a portion thereof, that were not replaced in the original series of 2D X-ray projections.

Figure 3:
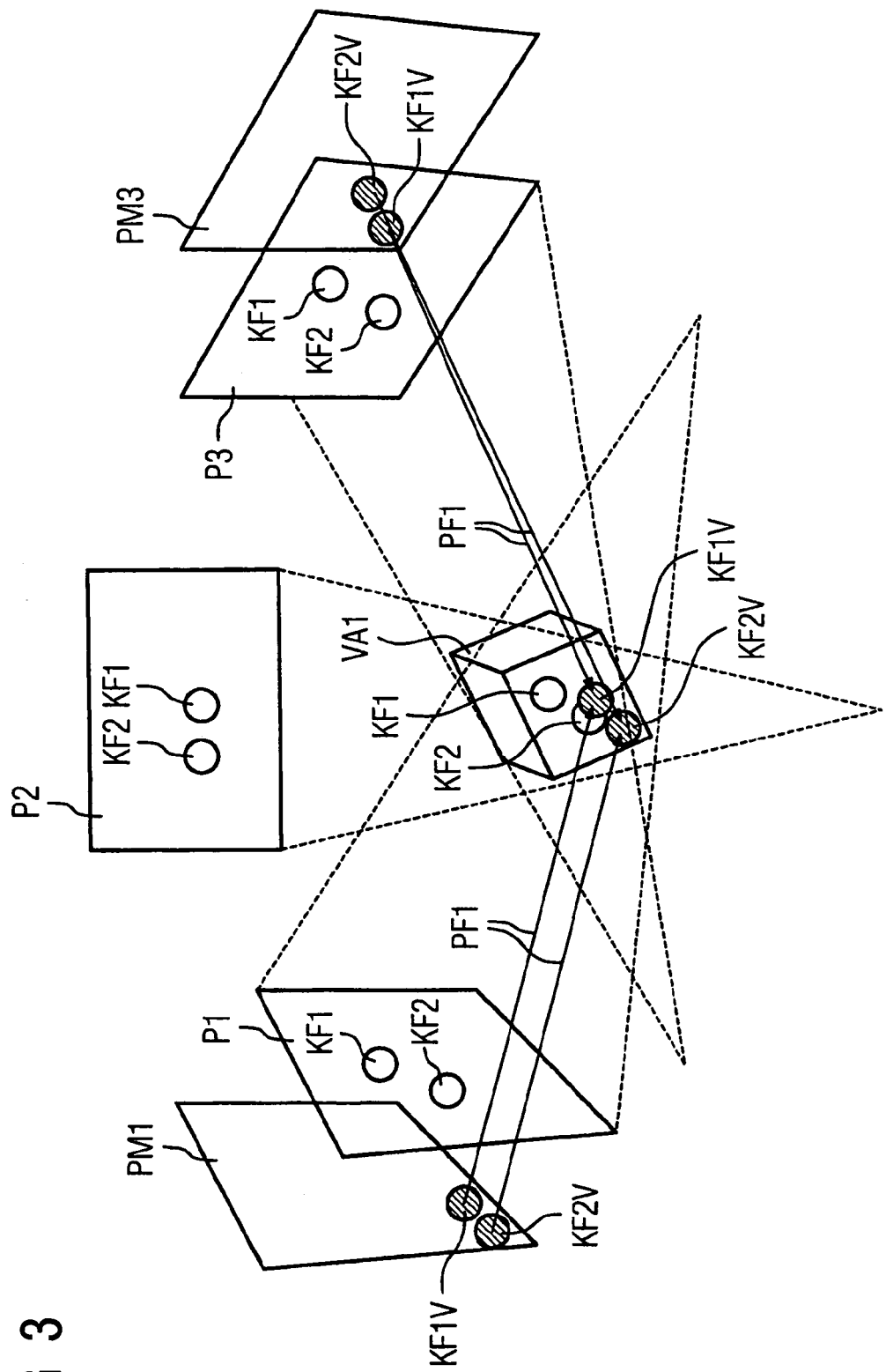
FIG. 3 schematically illustrates the generation of an updated volume dataset using m intraoperatively acquired 2D X-ray projections in accordance with the invention.

FIG. 3 schematically illustrates this procedure. FIG. 3 shows how the intraoperatively acquired 2D X-ray projection PM1 replaces the 2D X-ray projection P1 from the original series of n 2D X-ray projections. Likewise, the intraoperative 2D X-ray projection PM3 replaces the X-ray projection P3 from the original series of n 2D X-ray projections. The 2D X-ray projection PM1 and the 2D X-ray projection PM3 contain images KF1V and KF2V of bone fragments that are already imaged in the 2D X-ray projections P1 and P2. Comparison of the 2D X-ray projections reveals that the position of the bone fragments has changed in the course of the repositioning. Accordingly, as indicated in FIG. 3, the updated voxel volume VA1 resulting from the reconstruction contains both image information KF1, KF2 about the bone fragments in their initial position and orientation and, superimposed thereon, image information KF1V, KF2V about the bone fragments in their instantaneous position and orientation during the medical intervention. Although the image information KF1V, KF2V about the bone fragments in their altered position which is contained in the updated voxel volume VA1 and which derives from the few (e.g. m=5) intraoperatively acquired 2D X-ray projections, does not have the image sharpness of the bone fragments represented in their initial position, the imaging is sufficient for effectively supporting the surgeon in repositioning the bone fragments.

In order to be able better to distinguish the image information KF1, KF2 of the bone fragments in their initial position from the image information KF1V, KF2V of the bone fragments subsequent to their repositioning in the updated voxel volume VA1, the information can be gray scale coded or color coded.

This can be accomplished by subtracting the first voxel volume V1 from the updated voxel volume VA1, color coding the resulting voxel volume, which substantially comprises only image information of the bone fragments after their position change, and fusing said voxel volume with the first voxel volume V1 so as to generate a modified updated voxel volume. In this modified updated voxel volume, the image information KF1, KF2 of the bone fragments in their original position and orientation is consequently gray scale coded, and the image information KF1V, KF2V of the bone fragments in their instantaneous position and orientation during the intervention is color coded.

In the second embodiment of the inventive method, a second voxel volume is first reconstructed from the m 2D X-ray projections of the knee region K of the patient P that were acquired intraoperatively from m different projection angles, by back-projection with the m 2D X-ray projections. As described above, the C-arm 8 is moved into positions relative to patient P during the capturing of the m 2D X-ray projections in which 2D X-ray projections of the series of n 2D X-ray projections have already been acquired, so that the projection geometries for the m 2D X-ray projections are known and can be used directly for the reconstruction of the second voxel volume. Next, the first voxel volume V1 is fused with the second voxel volume that was reconstructed from the m 2D X-ray projections into an updated voxel volume VA2 containing information that is comparable to the voxel volume VA1, for which reason the voxel volumes VA1 an VA2 are not distinguished in the representation in FIG. 3. Accordingly, like the voxel volume VA1, the voxel volume VA2 contains image information KF1, KF2 of the bone fragments in their initial position and image information KF1V, KF2V of the bone fragments after repositioning. Because the number m of 2D X-ray projections that were used for the reconstruction is relatively small compared to the number n, the second reconstructed voxel volume has a poorer quality and resolution. However, these projections are sufficient for the three-dimensional representation of the repositioned bone fragments in their instantaneous position and orientation for purposes of supporting the medical intervention. The utilization of only a few 2D X-ray projections can accelerate the pick-up process and the reconstruction of the second voxel volume significantly, while appreciably reducing the radiation load on the patient P.

In the second embodiment of the method as well, in order to be able better to distinguish the image information of the bone fragments in their initial position from the image information of the bone fragments after repositioning in the updated voxel volume VA2, the information is represented in coded form. In the second embodiment of the method, this can be achieved by the image information of the bone fragments after repositioning being color coded in the second voxel volume prior to fusion of the first voxel volume with the second by means of the image computer 12, and the fusion with the first voxel volume V1 by the image computer 12 being performed only subsequent to this coding. Thus, a modified updated voxel volume is generated in which the image information of the bone fragments in their original position and orientation is gray scale coded, and the image information of the bone fragments in their instantaneous position and orientation during the intervention is color coded.

As previously mentioned for both versions, it is proven to be advantageous when, in an intraoperative acquisition of one of the m 2D X-ray projections, the C-arm 8 occupies a position relative to the patient P that is substantially the same as in the acquisition of a 2D X-ray projection of the series of n 2D X-ray projections, since in this case for the m 2D X-ray projection the projection geometries necessary for the back-projection are known. The movement to such an position can be achieved, for example, by automatically moving the C-arm 8 to such a position via an input from an operator console 15 indicated in FIG. 1, provided with an input means. In FIG. 1, an electromotor 16 controllable from the operator console 15 is shown for the orbital adjustment of the C-arm 8 along its perimeter in the positioner 7. Via a corresponding procedure at the operator console 15, the C-arm 8 can be subsequently automatically moved in each position that the C-arm 8 had occupied in the acquisition of any of the n 2D X-ray projections of the knee region K of the patient P. For the adjustment of the C-arm 8 around its angulation axis B, a corresponding electromotor (which is not shown in the FIG. 1) is provided that is also controllable from the operator console 15.

Movement of the C-arm 8 to a position in the intraoperative acquisition of a 2D X-ray projection, which corresponds to a position of the C-arm 8 in the acquisition of a 2D X-ray projection of the series of n 2D X-ray projections, alternatively can be achieved such that the C-arm 8 is manually adjusted by means of a handle shown in the FIG. 1, which ensues under the supervision of angle or position transmitters which are provided in FIG. 1 with the reference numbers 18 and 19.

In the intraoperative acquisition of one of the m 2D X-ray projections, a third possibility to bring the C-arm 8 into a position that the C-arm 8 had already occupied in the acquisition of a 2D X-ray projection of the series of n 2D X-ray projections is the use of a mechanical arresting device. In the exemplary embodiment, the mechanical arresting device has five bores 20 through 24 introduced into the C-arm 8 and a hook-shaped device 25 arranged at the positioner 7 which can be inserted into any one of the openings 20 through 24 to arrest the C-arm 8. In the exemplary embodiment, the hook-shaped device 25 is inserted into the opening 21 and thus arrests the C-arm 8 in a defined position that corresponds to a position that the C-arm 8 had previously occupied in the acquisition of a 2D X-ray projection of the series of n 2D projections.

It is of course possible in the intraoperative acquisition of 2D X-ray projections, for the C-arm 8 to occupy positions relative to the patient P, or the knee region K of the patient P, other than those occupied in the acquisition of the 2D X-ray projections of the series of n 2D X-ray projections. In this case, however, the projection geometries for these positions of the C-arm 8 must either be determined in a separate calibration process before the actual patient measurement, for example with the X-ray calibration phantom specified in German OS 100 47 382, or the projection geometries are calculated for the C-arm 8 at these positions by the image computer 12 by means of interpolation of the already known or determined projection geometries.

Insofar as the projection geometries for these positions of the C-arm 8 are known, in the first version of the inventive method a voxel volume can be reconstructed in a known way using these projection geometries, based on the m intraoperative 2D X-ray projections and the n–m 2D X-ray projections, or a portion thereof, that were not replaced.

In the second version of the inventive method, once the projection geometries have been determined, the second voxel volume can be reconstructed by the image computer 12 in a known manner and subsequently fused with the first voxel volume.

The versions of inventive method have been explained in the example of a movable C-arm X-ray device. The method can be implemented not only with movable C-arm X-ray devices, but also with stationary C-arm X-ray devices or other X-ray devices with which the generation of a volume dataset is possible from 2D X-ray projections.

Furthermore, the inventive method was explained in the context of the repositioning of bone fragments. However, the method is not only applicable to the repositioning of bone fragments, can be used with volume datasets of other types of biological tissue, or even other objects within the body of a patient, to update images after position changes of the biological tissue or the object.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for intraoperatively generating and updating a volume dataset, comprising the steps of:
   (a) before conducting a medical procedure involving a patient, acquiring a series of n 2D X-ray projections of biological tissue of the patient respectively at n different projection angles with an X-ray system, each of said projections having an associated projection geometry selected from the group consisting of known projection geometries and determinable projection geometries;
   (b) reconstructing a first volume dataset from said n 2D X-ray projections using said associated projection geometries;
   (c) after acquiring said series of 2D X-ray projections, intraoperatively acquiring m 2D X-ray projections of the patient during said medical procedure, from m different projection angles with said X-ray system, wherein m<n;
   (d) determining respective projection geometries for said intraoperatively acquired m 2D X-ray projections;
   (e) replacing m 2D X-ray projections in said series n 2D X-ray projections with said intraoperatively acquired m 2D X-ray projections, thereby leaving n–m 2D X-ray projections that were not replaced in said series of n 2D X-ray projections; and (f) reconstructing an updated volume dataset using said intraoperatively acquired m 2D X-ray projections and at least some of said n–m 2D X-ray projections.

2. A method as claimed in claim 1 wherein step (a) comprising acquiring said series of n 2D X-ray projections of said biological tissue in an initial position, and wherein said biological tissue is subsequently changed in position to a changed position, and wherein step (f) comprises reconstructing said updated volume dataset so as to contain image information of said biological tissue in said initial position and after the biological tissue has changed to said changed position.

3. A method as claimed in claim 2 comprising differently coding said image information representing said biological tissue in said initial position and the image information representing said biological tissue in said changed position, allowing the respective image information to be visually distinguishable.

4. A method as claimed in claim 3 comprising selecting said coding from the group consisting of gray scale coding and color-coding.

5. A method as claimed in claim 2 comprising the additional steps of subtracting said first volume dataset from said updated volume dataset to obtain a third volume dataset comprising only image information of said biological tissue in said changed position, and coding said third volume dataset to produce a coded third volume dataset, and fusing said coded third volume dataset with said first volume dataset to form a modified updated volume dataset.

6. A method as claimed in claim 2 wherein steps (a) and (c) comprise acquiring said series of n 2D x-ray projections and said series of m 2D x-ray projections of bone fragments, as said biological tissue.

7. A method as claimed in claim 1 comprising positioning said x-ray system in step (c) for acquiring said series of m 2D x-ray projections at respective positions that are substantially the same as respective positions of said x-ray system for acquiring said series of n 2D x-ray projections in step (a).

8. A method as claimed in claim 7 comprising automatically bringing said x-ray system to said same positions by a motor drive of said x-ray system.

9. A method as claimed in claim 7 comprising manually bringing said x-ray system to said same positions with electronic monitoring from at least one of angle transmitters and position transmitters.

10. A method as claimed in claim 7 comprising bringing said x-ray system to said same positions using a mechanical arresting mechanism that interacts with said x-ray system.

11. A method as claimed in claim 1 comprising positioning said x-ray system in step (c) for obtaining said m 2D x-ray projections at positions that are respectively different from positions of said x-ray system in step (a) for acquiring said series of n 2D x-ray projections, and wherein step (d) comprises obtaining said projection geometries respectively associated with said m 2D x-ray projections by calculation, in a calibration procedure, from said projection geometries in step (a).

12. A method as claimed in claim 1 comprising positioning said x-ray system in step (c) for obtaining said m 2D x-ray projections at positions that are respectively different from positions of said x-ray system in step (a) for acquiring said series of n 2D x-ray projections, and wherein step (d) comprises obtaining said projection geometries respectively associated with said m 2D x-ray projections by interpolation, from said projection geometries in step (a).

13. A method as claimed in claim 1 comprising employing a C-arm x-ray apparatus, having an x-ray source and a radiation receiver mounted on a C-arm, as said x-ray system in steps (a) and (c).

14. A method for intraoperative generation of an update volume dataset, comprising the steps of:
(a) acquiring a series of n 2D X-ray projections of biological tissue of a patient from n different projection angles with an X-ray system, each of said projections having an associated projection geometry selected from the group consisting of known projection geometries and determinable projection geometries;
(b) reconstructing a first volume dataset from said n 2D X-ray projections using said associated projection geometries;
(c) intraoperatively acquiring m 2D X-ray projections of the patient from m different projection angles with said X-ray system, wherein m<n;
(d) determining respective projection geometries for said intraoperatively acquired m 2D X-ray projections;
(e) reconstructing a second volume dataset using said intraoperatively acquired m 2D X-ray projections and the projection geometries that were determined in step (d) and
(f) fusing said first volume dataset with said second volume dataset to form an updated volume dataset.

15. A method as claimed in claim 14 wherein step (a) comprising acquiring said series of n 2D X-ray projections of said biological tissue of said patient in an initial position, and wherein said biological tissue is subsequently changed in position to a changed position, and wherein step (f) comprises reconstructing said updated volume dataset so as to contain image information of said biological tissue in said initial position and after said biological tissue has changed to said changed position.

16. A method as claimed in claim 15 comprising differently coding said image information representing said biological tissue in said initial position and said image information representing said biological tissue in said changed position, allowing the respective image information to be visually distinguishable.

17. A method as claimed in claim 15 comprising differently coding said information with a coding selected from the group consisting of gray scale coding and color-coding.

18. A method as claimed in claim 15 comprising coding said image information selected for said biological tissue in said changed position in said second volume dataset prior to fusing said first volume dataset with said second volume dataset.

19. A method as claimed in claim 15 wherein steps (a) and (c) comprise acquiring said series of n 2D x-ray projections and said series of m 2D x-ray projections of bone fragments, as said biological tissue.

20. A method as claimed in claim 14 comprising positioning said x-ray system in step (c) for acquiring said series of m 2D x-ray projections at respective positions that are substantially the same as respective positions of said x-ray system for acquiring said series of n 2D x-ray projections in step (a).

21. A method as claimed in claim 20 comprising automatically bringing said x-ray system to said same positions by a motor drive of said x-ray system.

22. A method as claimed in claim 20 comprising manually bringing said x-ray system to said same positions with electronic monitoring from at least one of angle transmitters and position transmitters.

23. A method as claimed in claim 20 comprising bringing said x-ray system to said same positions using a mechanical arresting mechanism that interacts with said x-ray system.

24. A method as claimed in claim 14 comprising positioning said x-ray system in step (c) for obtaining said m 2D x-ray projections at positions that are respectively different from positions of said x-ray system in step (a) for acquiring said series of n 2D x-ray projections, and wherein step (d) comprises obtaining said projection geometries respectively associated with said m 2D x-ray projections by calculation, in a calibration procedure, from said projection geometries in step (a).

25. A method as claimed in claim 14 comprising positioning said x-ray system in step (c) for obtaining said m 2D x-ray projections at positions that are respectively different from positions of said x-ray system in step (a) for acquiring said series of n 2D x-ray projections, and wherein step (d) comprises obtaining said projection geometries respectively associated with said m 2D x-ray projections by interpolation, from said projection geometries in step (a).

26. A method as claimed in claim 14 comprising employing a C-arm x-ray apparatus, having an x-ray source and a radiation receiver mounted on a C-arm, as said x-ray system in steps (a) and (c).

* * * * *